(12) United States Patent
Lin (10) Patent No.: US 9,370,575 B2
(45) Date of Patent: Jun. 21, 2016

(54) COMPOSITION FOR USE IN TREATING AND PREVENTING INFLAMMATION RELATED DISORDER

(75) Inventor: Shyh-Shyan Lin, Taipei (TW)

(73) Assignee: Aihol Corporation, Las Vegas, NV (US)

( * ) Notice: Subject to any disclaimer, the term of this patent is extended or adjusted under 35 U.S.C. 154(b) by 0 days.

(21) Appl. No.: 13/992,772

(22) PCT Filed: Jul. 2, 2012

(86) PCT No.: PCT/US2012/045238
§ 371 (c)(1),
(2), (4) Date: Jun. 10, 2013

(87) PCT Pub. No.: WO2013/006548
PCT Pub. Date: Jan. 10, 2013

(65) Prior Publication Data
US 2014/0141077 A1    May 22, 2014

(30) Foreign Application Priority Data

Jul. 7, 2011   (EP) .................................... 11173000

(51) Int. Cl.
*A61K 47/36* (2006.01)
*A61K 9/02* (2006.01)
(Continued)

(52) U.S. Cl.
CPC ............... *A61K 47/36* (2013.01); *A61K 31/606* (2013.01); *A61K 31/728* (2013.01); *A61K 45/06* (2013.01); *A61K 9/02* (2013.01); *Y10S 424/15* (2013.01)

(58) Field of Classification Search
None
See application file for complete search history.

(56) References Cited

U.S. PATENT DOCUMENTS 5,095,037 A   3/1992   Iwamitsu et al.
5,811,410 A * 9/1998   Falk et al. ...................... 514/54
(Continued)

FOREIGN PATENT DOCUMENTS

CN    102114031    4/2013
EP      2289522    3/2011
(Continued)

OTHER PUBLICATIONS

M Ahuja, AS Dhake, SK Sharma, DK Majumdar. "Topical Ocular Delivery of NSAIDs." The American Association of Pharmaceutical Scientists Journal, vol. 10 No. 2, Jun. 2008, pp. 229-241.*

(Continued)

*Primary Examiner* — Isaac Shomer
(74) *Attorney, Agent, or Firm* — Fishman & Associates, LLC.

(57) ABSTRACT

The present invention is related to a use for treating and preventing inflammation related disorder of a composition containing a drug and hyaluronic acid (HA) or HA mixture, whereas the HA or the HA mixture as a delivery vehicle can be a formulation including at least two HAs having different average molecular weights. The composition has been demonstrated to be capable of reducing the therapeutic dose of a drug on the treatment and prevention of inflammation related disorders is acute inflammatory disease, chronic obstructed pulmonary disease, coeliac disease, conjunctivitis, otitis, allergic rhinitis, gingivitis, aphthous ulcer, bronchitis, gastroesophageal reflux disease (GERD), esophagitis, gastritis, enteritis, peptic ulcer, inflammatory bowel disease (IBD), Crohn's Disease, irritable bowel syndrome (IBS), intestinal inflammation or allergy, urethritis, cystitis, vaginitis, proctitis, eosinophilic gastroenteritis, or rheumatoid arthritis.

6 Claims, 5 Drawing Sheets

(51) Int. Cl.
*A61K 31/728* (2006.01)
*A61K 45/06* (2006.01)
*A61K 31/606* (2006.01)

(56) References Cited

U.S. PATENT DOCUMENTS

| | | | |
|---|---|---|---|
| 5,869,471 A | | 2/1999 | Hovancik et al. |
| 6,107,347 A | * | 8/2000 | Francese et al. ............... 514/772 |
| 6,159,955 A | * | 12/2000 | Asculai et al. .................. 514/54 |
| 2002/0035075 A1 | * | 3/2002 | Borody .................. A61K 39/04 514/28 |
| 2002/0198141 A1 | * | 12/2002 | McChesney et al. ............. 514/6 |
| 2003/0045553 A1 | * | 3/2003 | Bussolari et al. ............. 514/340 |
| 2003/0055028 A1 | * | 3/2003 | Stergiopoulos et al. ...... 514/179 |
| 2004/0019011 A1 | * | 1/2004 | Falk et al. ....................... 514/54 |
| 2005/0159396 A1 | * | 7/2005 | Harty .................... A61K 31/13 514/166 |
| 2005/0260193 A1 | * | 11/2005 | Lieberburg ................ 424/130.1 |
| 2008/0025986 A1 | * | 1/2008 | Ozes et al. ................. 424/145.1 |
| 2009/0143331 A1 | | 6/2009 | Strompoulis et al. |
| 2011/0166100 A1 | | 7/2011 | Wu |

FOREIGN PATENT DOCUMENTS

| | | | |
|---|---|---|---|
| EP | 2292243 | | 3/2011 |
| JP | H061281259 | | 5/1994 |
| JP | 2009543873 | | 12/2009 |
| JP | 2011037853 | | 2/2011 |
| JP | 2011037853 A | * | 2/2011 |
| WO | 03033004 | | 4/2003 |

OTHER PUBLICATIONS

L Laine, DM Jensen. "Management of Patients with Ulcer Bleeding." The American Journal of Gastroenterology, vol. 107, Mar. 2012, pp. 345-360.*

University of Maryland Medical Center. "Crohn's Disease." http://unm.edu/health/mecical/aitmedlcoodition/crahns-disease, accessed May 15, 2014. 14 printed pages.*

WebMD. "Irritable Bowel Syndrome (IBS) Health Center." http://www.webmd.com/ibs/guide/irritable-bowel-syndrome-ibs-prevention, accessed May 15, 2014. 2 printed pages.*

WebMD. "Allergies Health Center Allergic Rhinits—Prevention." http://www.webmd.com/allergies/tc/allergic-rhinitis-prevention, accessed May 15, 2014, 2 printes pages.*

CA Cooper, KK Brown, CD Meletis, N Zabriskie. "Inflammation and Hyaluronic Acid." Alternative & Complementary Therapies, Apr. 2008, pp. 78-84.*

RJ Peach, D Hollenbaugh, I Stamenkovic, A Aruffo. "Identification of Hyaluronic Acid Binding Sites in the Extracellular Domain of CD44." The Journal of Cell Biology, vol. 122, No. 1 Jul. 1993, pp. 257-264.*

A Neumann, R Schinzel, D Palm, P Riederer, G Munch. "High molecular weight hyaluronic acid inhibits advanced glycation endproduct-induced NF-kB activation and cytokine expression." FEBS Letters, vol. 453, 1999, pp. 283-287.*

E Gullberg, JD Soderholm. "Peyer's Patches and M Cells as Potential Sites of the Inflammatory Onset in Crohn's Disease." Annals of the New York Academy of Sciences, vol. 1072, 2006, pp. 218-232.*

Machine Translation of Wu (JP 2011037853 A). Patent published in Japanese on Feb. 24, 2011, translation obtained by examiner on Jun. 10, 2015. 25 printed pages.*

Supreme Court of the United States. "*Mayo Collaborative Services, DBA Mayo Medical Laboratories, et al.* v. *Prometheus Laboratories, Inc.*" Mar. 20, 2012, pp. 1-4 and 1-24 (28 total printed pages).*

E Esposito, E Menegatti, R Cortesi. "Hyaluronan-based microspheres as tools for drug delivery: a comparative study." International Journal of Pharmaceutics, vol. 288, 2005, pp. 35-49.*

P Kedia, RD Cohen, "Once-daily MMX mesalamine for the treatment of mild-to-moderate ulcerative colitis." Therapeutics and Clinical Risk Management, vol. 3(5), 2007, pp. 919-927.*

Chemical Abstracts. CAS Registry Record for Mesalamine (CAS# 89-57-6). entered STN Nov. 16, 1984, 6 printed pages.*

Sufiyarov, I.F., "Experimental Validation for the Use of a Film on the Basis of Modified Hyaluronic Acid for Prevention of Postoperative Peritoneal Adhesions", Bulletin of Experimental Biology and Medicine, (2007), vol. 144, No. 2, pp. 269-271, Springer Science+Business Media, Inc.

Ossipov, Dmitri A., "Nanostructured Hyaluronic Acid-Based Materials for Active Delivery to Cancer", Expert Opinion on Drug Delivery, (2010), vol. 7, No. 6, pp. 681-703, Uppsala University, Polymer Chemistry, Material Chemistry Department, S-75121 Uppsala, Sweden.

* cited by examiner

COMPOSITION FOR USE IN TREATING AND PREVENTING INFLAMMATION RELATED DISORDER

BACKGROUND OF THE INVENTION

1. Field of the Invention

The present invention provides a composition of hyaluronic acids in combination with a drug for treating and preventing an inflammation related disorder, especially where the onset of the disorder mainly occurs in mucosal tissue.

2. Description of the Prior Arts

Hyaluronic acid, also known as hyaluronan, hyaluronate and sodium hyaluronate, is generally referred to as HA, which is a natural glycosaminoglycan macromolecule including disaccharides composed of the alternative N-acetyl-D-glucosamine and D-glucuronic acid linked via alternative β-1,3 and β-1,4 glycosidic bonds. HA found in nature with a molecular weight (Mw) between 50,000 Dalton (Da) and a few millions Dalton usually has high viscosity.

HA found in nature is the extra-cellular material with elasticity, filling between the cells and the collagenous fibers and covering onto some epidermal tissues, mainly for protecting and lubricating cells, for providing a platform for transporting the regulatory T cell, and also for stabilizing collagen network and protecting collagen network from the mechanical damage. HA is also a major lubricant in the tendon and the tendon sheath and on the surface of the synovial membrane due to the lubricant feature and the high shock absorber, and HA is helpful for the tissue rheological mechanics, motion and the cell proliferation (referring to Delpech, B. et al., 1997. Hyaluronan: fundamental principles and applications in cancer. *J Intern. Med.* 242, 41-48), and participates in the receptor interaction on the surface of some cells, particularly to be the major receptor of CD44. CD44 is widely accepted as a marker of the activated lymphocyte (referring to Teder P, et al., 2002, Resolution of lung inflammation by CD44. *Science*).

Recently, HA is applied in clinical treatment in the sodium salt form mainly in eye, skin, orthopedics, surgery, arthritis, artery treatment and in cosmetic fields. The HA with alkali metal ion, alkaline earth metal ion (for example, the magnesium ion), aluminum ion, ammonium ion, and salt form of the replacement of the ammonium ion can be the carrier for assisting drug absorption (referring to Belgium Patent 904, 547). The silver salt is used as the mycocide and the gold salt is used for treating the rheumatoid arthritis among the heavy metal salt of the HA (referring to WO 87/05517).

Anti-inflammatory refers to the property of a substance or treatment that reduces inflammation. Anti-inflammatory drugs make up about half of analgesics, remedying pain by reducing inflammation as opposed to opioids, which affect the central nervous system. The related drugs are described as follows:

1. Steroids, specifically glucocorticoids, reduce inflammation or swelling by binding to glucocorticoid receptors. These drugs are often referred to as corticosteroids.

2. Non-steroidal anti-inflammatory drugs (NSAIDs) alleviate pain by counteracting the cyclooxygenase (COX) enzyme. On its own, COX enzyme synthesizes prostaglandins, creating inflammation. In whole, the NSAIDs prevent the prostaglandins from ever being synthesized, which reduces or eliminates the pain. Some common examples of NSAIDs are: aspirin, ibuprofen, and naproxen. The newer specific COX-inhibitors, although it is presumed, sharing a similar mode of action, are not classified together with the traditional NSAIDs.

3. ImSAIDs were discovered to have diverse biological properties, including anti-inflammatory properties. ImSAIDs work by altering the activation and migration of inflammatory cells, which are immune cells responsible for amplifying the inflammatory response (Bao F, John S M, Chen Y, Mathison R D, Weaver L C. The tripeptide phenylalanine-(D) glutamate-(D) glycine modulates leukocyte infiltration and oxidative damage in rat injured spinal cord. *Neuroscience.*, 2006, 140(3):1011-22; Epub on 2006 Apr. 3). The ImSAIDs represent a new category of anti-inflammatory drugs and are unrelated to steroid hormones or non-steroidal anti-inflammatory drugs.

U.S. Pat. No. 6,159,955 discloses a method of treating aphthous ulcers comprising administration of an effective amount of a composition comprising a NSAID and a formulation of hyaluronic acid selected from hyaluronic acid, pharmaceutically acceptable salts thereof, fragments thereof and/or subunits thereof. However, it did not emphasize the less dose of the NSAID being used, whereas mesalamine does not belong to NSAID.

The mucous membranes (or mucosae; singular mucosa) are linings of mostly endodermal origin, covered in epithelium, and involved in absorption (gastrointestinal tract) and secretion (gastrointestinal and respiratory tract). They line cavities that are exposed to the external environment and internal organs and contiguous with skin at several body areas: at the nostrils, the mouth, the lips, the eyelids, the ears, the genital area, and the anus. The sticky, thick fluid secreted by the mucous membranes and glands is termed mucus. The term mucous membrane refers to where they are found in the body and not every mucous membrane secretes mucus.

Conjunctivitis refers to inflammation of the conjunctiva (the outermost layer of the eye and the inner surface of the eyelids).

Otitis is a general term for inflammation or infection of the ear, in both humans and other animals.

Rhinitis is defined as inflammation of the nasal membranes and is characterized by a symptom complex that consists of any combination of the following: sneezing, nasal congestion, nasal itching, and rhinorrhea. The eyes, ears, sinuses, and throat can also be involved. US patent application 20050107330 disclosed a pharmaceutical composition for curative topical treatment of rhinitis comprising at least one acidic glycosaminoglycan. But this invention also contains at least one sympathomimetic suitable for topical application and having vasoconstrictor action or detumescent action on the mucous membrane or its physiologically acceptable salts or derivatives. It did not disclose the technical concept that less dose of drug can be used in need by combining with HA.

Oral mucosa is the mucous membrane epithelium of the mouth. An oral ulcer is an open sore inside the mouth, or rarely a break in the mucous membrane or the epithelium on the lips or surrounding the mouth. Once formed, the ulcer may be maintained by inflammation and/or secondary infection.

Bronchitis is inflammation of the mucous membranes of the bronchi, the airways that carry airflow from the trachea into the lungs. Bronchitis can be divided into two categories, acute and chronic, each of which has unique etiologies, pathologies, and therapies. US patent application 20030171332 discloses a method of treating respiratory conditions by a polysaccharide capable of binding CD44. However, only one single species of HA could be involved and the prior art did not disclose a combination of HA and a drug, not to mention merely a less dose of drug being used.

The mucosa is the innermost layer of the gastrointestinal wall that is surrounding the lumen, or open space within the tube. This layer comes in direct contact with food bolus, and is responsible for absorption, digestion, and secretion which are the important processes in digestion.

Generally known as peptic ulcer, and also known as PUD or peptic ulcer disease, peptic ulcer is an ulcer (defined as mucosal erosions equal to or greater than 0.5 cm) of an area of the gastrointestinal tract that is usually acidic and thus causes extreme pain. Ulcers can also be caused or worsened by drugs such as aspirin, Plavix (clopidogrel), ibuprofen, and other NSAIDs (non-steroid anti-inflammatory drugs).

Mesalamine, also known as Mesalazine or 5-aminosalicylic acid (5-ASA), is an anti-inflammatory drug used to treat inflammation of the digestive tract ulcerative colitis and mild-to-moderate Crohn's disease. Mesalamine is a bowel-specific aminosalicylate drug that acts locally in the gut and has its predominant actions there, thereby having few systemic side effects. As a derivative of salicylic acid, mesalamine is also thought to be an antioxidant that traps free radicals, which are potentially damaging byproducts of metabolism. Mesalamine is considered the active moiety of sulfasalazine, which is metabolized to sulfapyridine and mesalamine (Lippencott's Illustrated Reviews: Pharmacology, 4th Ed. Finkel, Cubeddu and Clark). Mesalamine is formulated for oral ingestion as tablets or granules, and for rectal administration as a rectal suppository, suspension or enemas. The regular therapeutically effective dose of three commercial drugs of mesalamine is introduced herein. Retention enema rectally for adult with ulcerative proctitis (active, chronic) and proctosigmoiditis (active ulcerative): 4 gm retention enema rectally QD at bedtime (retain for 8 hours) for 3 to 6 weeks (Colasa®). For the treatment of mildly to moderately active ulcerative colitis: The usual dosage in adults is two 400-mg tablets to be taken three times a day for a total daily dose of 2.4 grams for a duration of 6 weeks (Asacol®). The recommended dosage for the induction of remission and the symptomatic treatment of mildly to moderately active ulcerative colitis is 1 g (4 PENTASA 250 mg capsules or 2 PENTASA 500 mg capsules) 4 times a day for a total daily dosage of 4 g. Treatment duration in controlled trials was up to 8 weeks. (PENTASA®). In a preferred embodiment, the drug is a steroid, prednisolone. The initial dose of prednisone varies depending on the condition being treated and the age of the patient. The starting dose may be from 5 to 60 mg per day and often is adjusted based on the response of the condition being treated (Prednesol®). In a preferred embodiment, the drug is a NSAID, Naproxen. For Rheumatoid arthritis, osteoarthritis, and ankylosing spondylitis: 250-500 mg Naproxen is administered orally twice daily and may be increased to 1.5 g/day of naproxen base for limited time period. (Naprosyn®).

With regards to interaction between molecules, intermolecular forces are first categorized into hydrogen bond and non-covalent bond. Hydrogen bonds are essentially electrostatic in nature, although the energy of hydrogen bond can be decomposed into additional contributions from polarization, exchange repulsion, charge transfer, and mixing. A hydrogen bond is the attractive force between a hydrogen atom and an electronegative atom, such as nitrogen, oxygen, or fluorine. The hydrogen bond is often described as a strong electrostatic dipole-dipole interaction. The most common hydrogen bonds in biological systems involve oxygen and nitrogen atoms.

As another kind of interaction between molecules, the non-covalent bond is the dominant type of interaction between supermolecules in supermolecular chemistry. Noncovalent bonds are critical in maintaining the three-dimensional structure of large molecules and are involved in many biological processes in which large molecules bind specifically but transiently to one another. The forces consist of four types: (1) dipole-dipole forces, (2) ion-dipole forces, (3) dipole-induced dipole force or Debye forces, and (4) instantaneous dipole-induced dipole forces or London dispersion forces. Molecular interactions are fundamentally electrostatic in nature and can be described by Coulomb's Law. Coulomb's law correctly describes forces that bind (1) electrons to nuclei in atoms, (2) atoms to atoms in molecules, and (3) molecules to molecules in liquids and solids. The detailed descriptions of such forces are common scientific knowledge which are omitted herein.

SUMMARY OF THE INVENTION

The objective of the present invention is to provide a composition for use in treating or preventing inflammation related disorder, which requires a lower dose of anti-inflammatory drug and thus fewer side-effects of said drug will occur once the composition is administrated to a subject suffering from inflammation related disorder.

Accordingly, the present invention provides a composition for use in treating or preventing an inflammation related disorder in a mammal or human comprising:

a drug suitable for the treatment of an inflammation in a dose less than the regular therapeutically effective dose thereof, and hyaluronic acid (HA) or HA mixture, whereby the HA or the HA mixture used as a delivery vehicle delivers the drug specially to the inflammatory tissue while the composition is administrated to the mammal or human suffering from the inflammation related disorder.

Other objectives, advantages and novel features of the invention will become more apparent from the following detailed description when taken in conjunction with the accompanying drawings.

The scenario of the present invention is based on the previous test results of the inventors, wherein the amount of hyaluronic acid (HA) binding onto the inflammatory surface was higher than in the non-inflammatory area. Further, the results of the present invention indicate that HA can be taken as a delivery vehicle to carry a drug suitable for the treatment of an inflammation and/or allergy, in a preferred embodiment, mesalamine. Notwithstanding the detailed mechanism between HA and mesalamine is still not so clear, the results of the present invention prove a composition comprising HA and mesalamine can sustain the concentration of mesalamine in the colon. Hereinafter will be the detailed description of the scenario.

Figure 1:
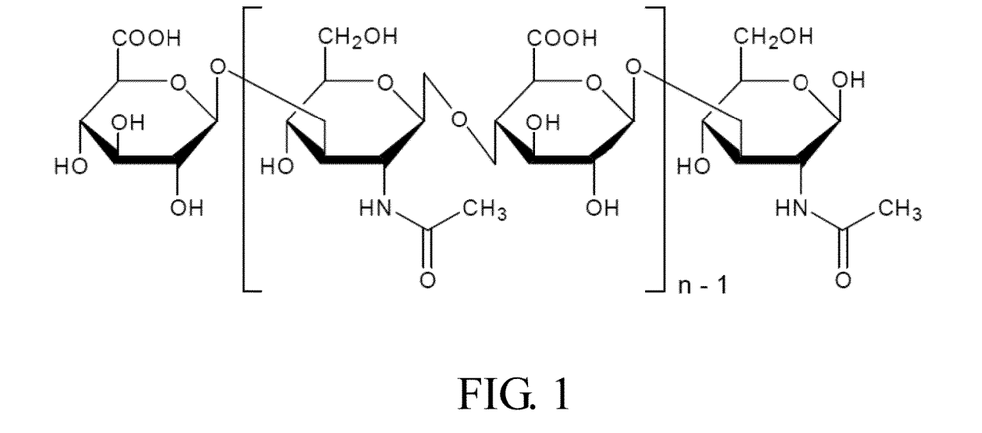
FIG. 1 shows the general chemical structure of the hyaluronic acid.

HA based on its repeated disaccharide units forms a linear structure (FIG. 1). However, in the high average Mw HA, by the reaction of HA with an amine, the carboxylic groups of the linear HA macromolecules react with the di/tri/poly amines in the same or other HA macromolecules to form an amide linkage and form an inter- or intra-molecular bridge. Due to this reaction, the starting coiled HA structure is transformed into a globular spherical nanoparticle (referring to U.S. Pat. No. 7,879,818). In a preferred embodiment of the present invention, a HA mixture has been set up comprising at least two species of HAs of different average molecular weights including low average molecular weight hyaluronic acid (LMWHA) and high average molecular weight hyaluronic acid (HMWHA). HAs of different molecular weights have different rheology, adhesion, functions as tissue scaffold and degradation properties in the solution.

HA hydrolysis catalyzed by HAase is believed to be involved in the control of the balance between longer and shorter HA chains. Shorter HA chains seem to be too short to form a stable complex and longer HA chains encounter difficulties in forming a complex, probably because of steric hindrance.

Pursuant to the present invention, on contrary to conventional techniques that one single species of HA is used for simple and regular situation, in a preferred embodiment the specific HA mixture provided by the inventors is also involved. The specific HA mixture comprises at least LMWHA and HMWHA. The HA with an average molecular weight lower than 1.5 million Da is categorized as LMWHA, the preferred range of the average molecular weight is between 50 kilo Da and 1.5 million Da, the more preferred range of the average molecular weight is between 0.1 million and 1.5 million Da, and the most preferred range of the average molecular weight is between 0.1 million and 0.5 million Da. The HA with an average molecular weight higher than 1.5 million Da is categorized as HMWHA, the preferred range of the average molecular weight is between 1.5 million and 5 million Da, and the most preferred range of the average molecular weight is between 1.5 million and 3.5 million Da. In a preferred embodiment, the average molecular weight of LMWHA is apart from the average molecular weight of HMWHA at least 0.5 million Da. The general chemical structure of the HA is illustrated as in FIG. 1.

Another preferred embodiment of the composition in accordance with the present invention includes, but not limited to, a 1:1 (w/w) mixture of LMWHA and HMWHA by weight in a salt form of HA, and a more preferred embodiment of the ratio of LMWHA to HMWHA may be adjusted depending on the clinical purpose to be between 20:80 and 80:20 by weight. The HA mixture with a higher ratio of LMWHA to HMWHA can be more helpful in speeding up the treatment; on the contrary, a higher ratio of HMWHA to LMWHA can provide a longer degradation rate to prolong the treatment effect.

The term mucosa used herein includes, but not limited to, the mucosa of an eye, the mucosa of an ear, the mucosa of a nose, the mucosa of a mouth, the mucosa of a respiratory tract, the mucosa of a gastrointestinal tract, the mucosa of a urinary tract and the mucosa of a genital tract. The preferred embodiment of the inflammation related disorder includes, but not limited to, acute inflammatory disease, chronic obstructed pulmonary disease, coeliac disease, conjunctivitis, otitis, allergic rhinitis, gingivitis, aphthous ulcer, bronchitis, gastroesophageal reflux disease (GERD), esophagitis, gastritis, enteritis, peptic ulcer, inflammatory bowel disease (IBD), Crohn's Disease, irritable bowel syndrome (IBS), intestinal inflammation or allergy, urethritis, cystitis, vaginitis, proctitis, eosinophilic gastroenteritis, or rheumatoid arthritis. The more preferred embodiment of peptic ulcer includes, but not limited to, gastric ulcer, duodenal ulcer, esophageal ulcer and Meckel's Diverticulum ulcer. The more preferred embodiment of IBD includes, but not limited to, Crohn's disease and ulcerative colitis. The more preferred embodiment of IBS includes, but not limited to, coeliac disease, fructose malabsorption, mild infections, parasitic infections like giardiasis, functional chronic constipation and chronic functional abdominal pain. The result of the present invention shows that HA is absorbed in the injured colon tissues obviously higher than in the normal colon tissues (P<0.01, FIG. 2). Comparing the differences among HAs of three average molecular weights absorbed in the injured colon tissues, the fluorescent index of absorption of 350 K Da HA by the injured colon tissues was obviously higher than HAs of the other two average molecular weights (2 M Da and 1 M Da). Further, the fluorescent index of absorption of 1 M Da HA by even normal or injured colon tissues was higher than 2 M Da HA. This result explains fast dispersed and covered effect of low Mw HA which supplies instant wound healing and protection of the tissue from being injured further.

Another preferred embodiment of the composition of the present invention includes a HA or a HA mixture including an excipient to formulate an administrating dosage form for eye, ear, oral, nose, respiratory tract, gastrointestinal tract or topical use. The more preferred embodiment of the oral dosage form is selected from the group consisting of solid dosage form, solution including, but not limited to suspension, tablet including, but not limited to controlled-release tablet, and capsule including, but not limited to enteric-coated capsule. The more preferred embodiment of the gastrointestinal tract administration form is selected from the group consisting of solid dosage form, perfusion, enema, suppository, and solution including, but not limited to, suspension. The more preferred embodiment of the topical administration form is selected from the group consisting of perfusion, enema, suppository, spray, inhalation, and drop.

According to the present invention, the drug suitable for the treatment of an inflammation of the present invention includes the steroid, non-steroid anti-inflammatory drug (NSAID), mesalamine and derivatives thereof.

The preferred embodiment of treating allergic rhinitis or bronchitis can be carried out by administrating the composition of the present invention involving a drug of antihistamine, anti-allergics, anticongestives, steroid or antiasthma to a subject in need thereof. The preferred embodiment of treating enteritis can be carried out by administrating the composition of the present invention involving a drug of antibiotic or antispasmodic to a subject in need thereof. The preferred embodiment of treating peptic ulcer can be carried out by administrating the composition of the present invention involving a drug of coagulant, antibiotics, antacid, H2 blocker, potassium hydrogen ion pump blocker (PPI), cytoprotectives or mucosa protector to a subject in need thereof. The preferred embodiment of treating IBD can be carried out by administrating the composition of the present invention involving a drug of steroid, immunosuppressive agent, antibiotic, 5-aminosalicylic acid (5-ASA) and derivatives, or anti-inflammatory to a subject in need thereof.

The preferred embodiment of treating IBS can be carried out by administrating the composition of the present invention involving a drug of antiallergic, antispasmodic, antidiarrheal, neurolytic, tranquilizer, narcotic analgesic, antidepressant or serotonin antagonist to a subject in need thereof. In a more preferred embodiment, the drug in the composition of the present invention includes the antihistamine, anti-allergy, anti-inflammatory, immuno-suppressant, or combination thereof.

In the preferred embodiment of oral formulation (for example, enteric coated tablet), the enteric coating provides more resistance dissolution and digestion in the stomach, and after reaching the intestine and colon, the enteric coating will be dissolved and the HA herein will be released to form a protection membrane at the inflammatory colon (the region of ascending or transverse colon).

In the preferred embodiment of suppository formulation, the suppository containing the composition herein may be inserted into the anus and the composition will dissolve in the rectum and spread to other regions of the colon (for example the descending region) to form a protection membrane at the inflammatory colon.

In the preferred embodiment of perfusion formulation (for example, enema), the HA or mixture of HAs in the composition herein is the major active ingredient mixed with the excipient (for example, phosphate buffered saline (PBS solution or suspension formulation)) directly used or in a soft tube to inject the above composition into the colon. The composition will be charged into the colon and spread to other regions of colon (for example, the descending region) to form a protection membrane at the inflammatory colon and to treat inflammation by the drug.

The more preferred embodiment of the subject being treated by the composition used herein is mammal. The most preferred embodiment of the subject is human.

The composition of the present invention is made by natural physical or chemical force. The intermolecular force between the HA and a drug of the present invention most probably is chelation, electrostatic interaction or adhesion. Chelation is the formation or presence of two or more separate coordinate bonds between a polydentate (multiple bonded) ligand and a single central atom. Usually these ligands are organic compounds. Though all molecular interactions are inherently electrostatic in nature, electrostatic interaction usually specifically represents any of the attractive or repulsive forces between atoms and/or groups of atoms and/or molecules that are due to the presence of ionized chemical entities and to the electronegative and electropositive properties of these atoms, groups, or molecules. Adhesion is any attraction process between dissimilar molecular species that can potentially bring them into "direct contact". Adhesion is the tendency of dissimilar particles and/or surfaces to cling to one another.

In a preferred embodiment, the drug may be enclosed or coated by HA or HA mixture aforementioned to form a polymer or a globular enclosure. Under this situation, either HA itself or an excipient added can keep a certain amount of the drug and make the drug work efficiently on the inflammatory region.

Figure 2:
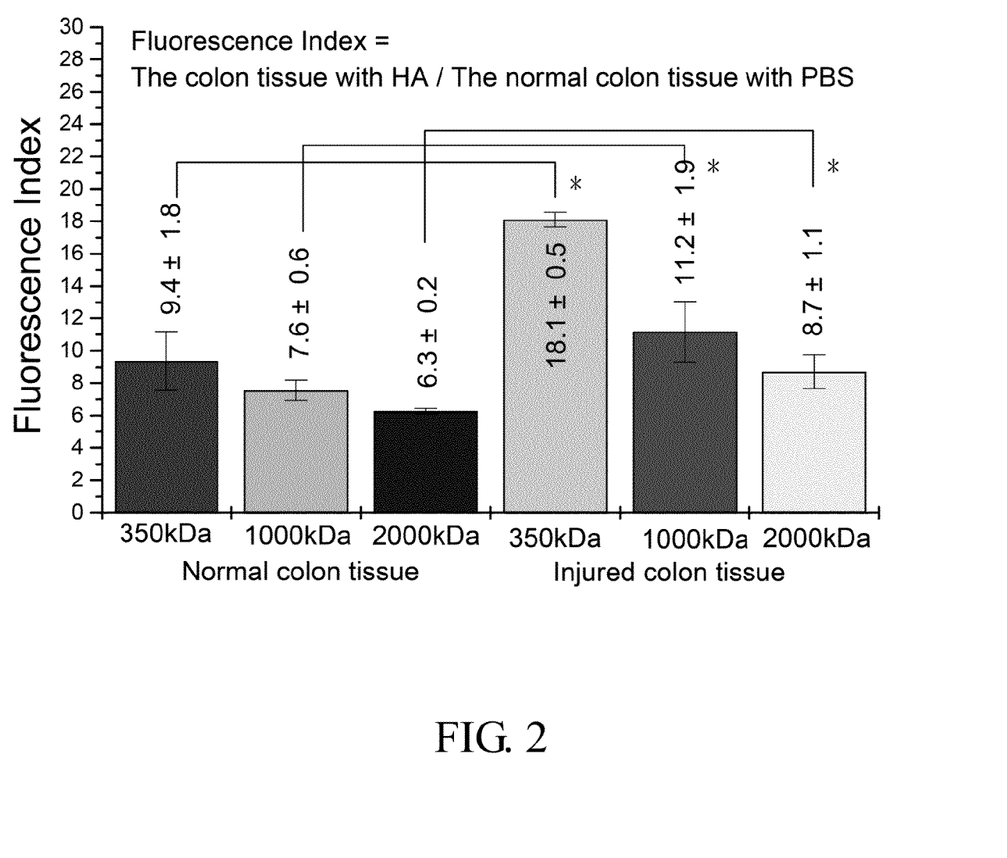
FIG. 2 shows the affinity of HAs by fluorescent index in normal and injured colon tissues (*p<0.05)
Figure 3:
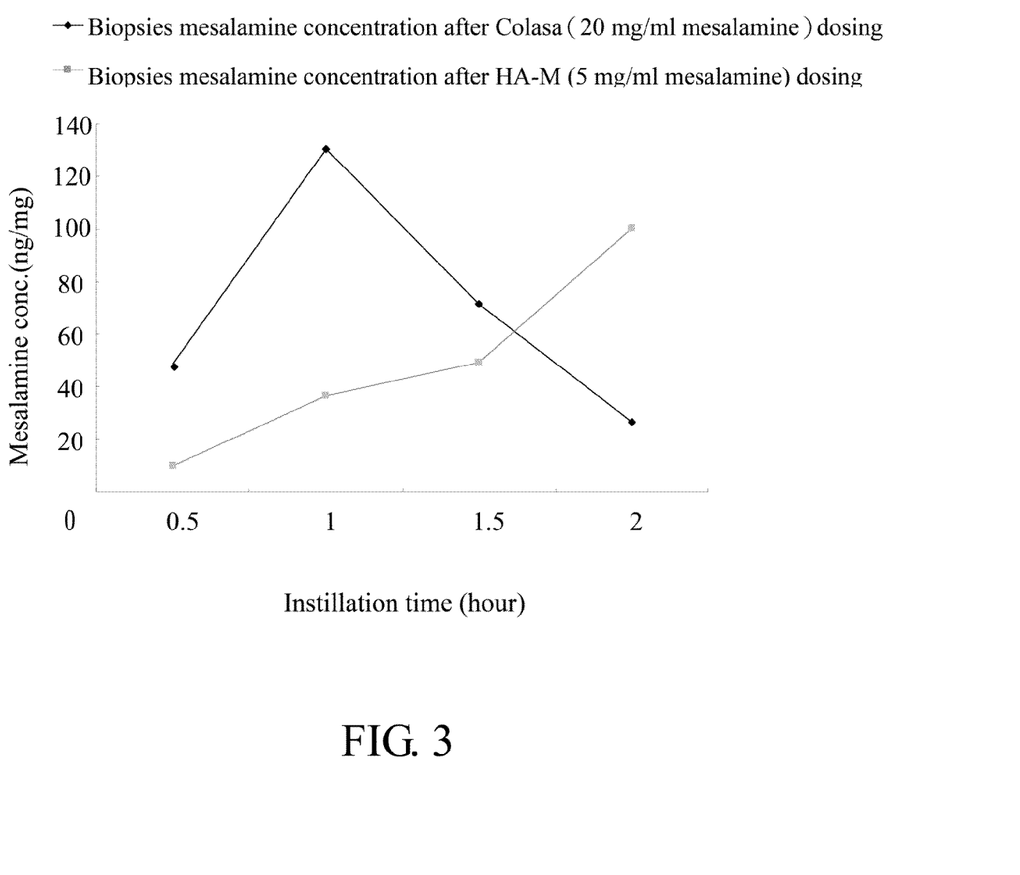
FIG. 3 shows colon tissue biopsies time, mesalamine concentration profile after Colasa® (a brand of enema preparation with 20 mg of mesalamine in 1 ml solution) or HA-mesalamine dosing.
Figure 4:
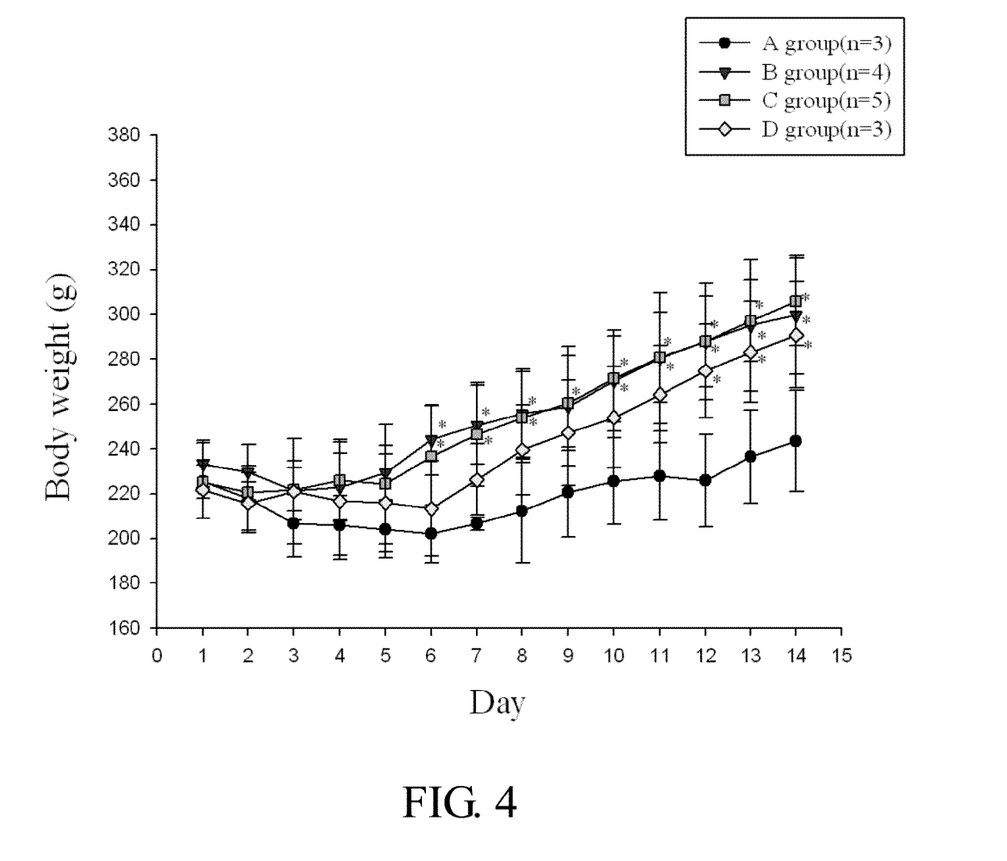
FIG. 4 shows comparison of the effect of mesalamine and HA-mesalamine with control group in treating IBD indicated by average body weight of rats (mean±SD) through test days 1 to 14 (*p<0.05 vs. group A)
Figure 5:
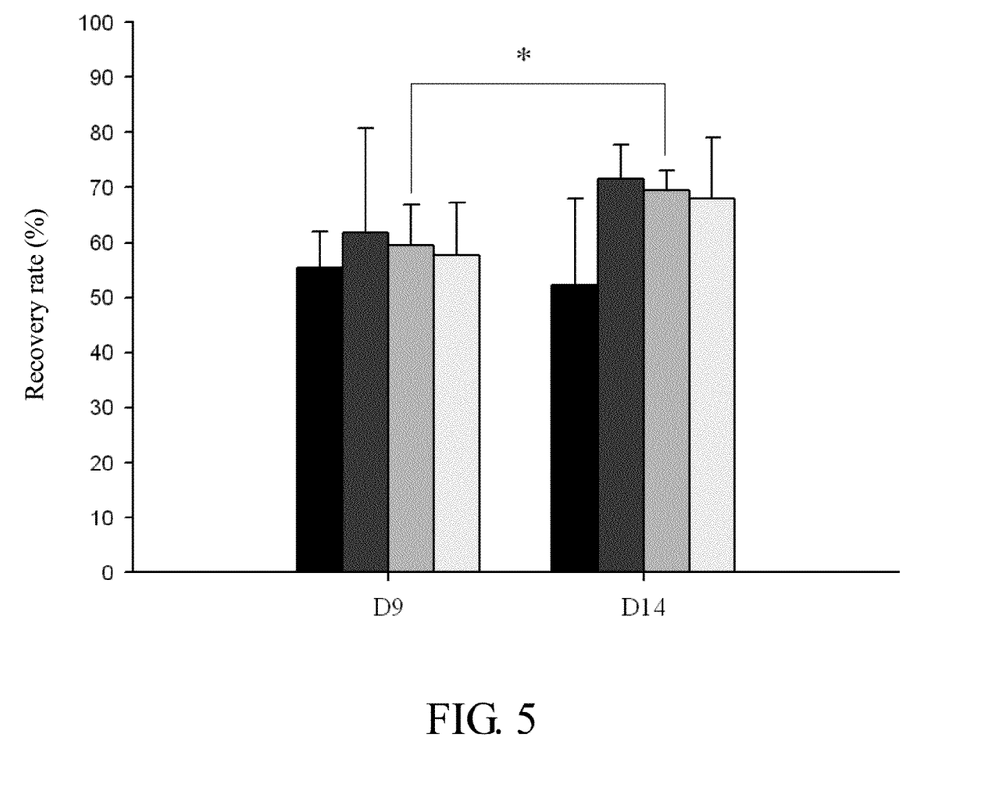
FIG. 5 shows comparison of the effect of mesalamine and HA-mesalamine with control group in treating IBD indicated by recovery rate of rats (mean±SD) between test day 9 (D9) and day 14 (D14) (*p<0.05 vs. group A).

The biggest contribution of the present invention is providing a composition of a HA formulation with a drug which can significantly decrease the therapeutic dose of the drug. Because the doses of different drugs depend upon various situations of different patients, the present invention only provides preferred embodiments to be a representative. The preferred embodiment of the drug of the present invention is mesalamine, a drug known for treating IBD. The result of the present invention shows that only one-fourth of the regular therapeutically effective dose was used, but having almost the same efficacy to ameliorate the inflammation of artificially induced IBD in rats. In a more preferred embodiment, one-eighth of the regular therapeutically effective dose was used in the present invention. Another preferred embodiment is that HA prefers to recognize and attach to the inflammatory region (FIG. 2). In a preferred embodiment, when only one species of HA is utilized instead of a HA mixture aforementioned containing at least two species of HAs, its average molecular weight is between 50 kilo Dalton and 5 million Dalton. Though the actual mechanism of intermolecular force between HA and drug is still not so clear, the present invention has provided several evidences that mixing HA and mesalamine can contribute to the combination of each advantage of both, confirmed by the results of Example 2 below as shown in FIG. 3 and those of Example 3 below as shown in FIGS. 4 and 5. The technical concept combining HA with a special guidance ability (as a delivery vehicle) to inflammatory region and a drug with less dose has never been disclosed till the present invention, especially HA by itself also has ability to treat inflammation. Therefore, the present invention provides a clever, easy, simple way to save the drug dose and concentrate the effect of the drug on inflammatory region. A preferred embodiment of the present invention is acting on the mucosal tissue because of the characteristic of HA. Preferably, the present invention reduces the dose and/or amount required of the drug and thence decreases the cost on drug.

Another preferred embodiment of the present invention is providing a method for treating or preventing inflammation and/or allergy related disorder comprising administering to a mammal or human in need thereof a composition of a drug suitable for the treatment of an inflammation and/or allergy in a dose less than regular therapeutically effective dose and hyaluronic acid (HA), wherein the HA used as a delivery vehicle to deliver the drug specially to the inflammatory tissue.

According to the present invention, the drug suitable for the treatment of an inflammation and/or allergy is steroid, non-steroidal anti-inflammatory drugs (NSAIDs), immune selective anti-inflammatory derivatives (ImSAIDs) or mesalamine.

More preferably, the drug suitable for the treatment of an inflammation and/or allergy is, for example, but not limited to, mesalamine, 5-aminosalicylate, sulfasalazine and olsalazine, aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, alpha.-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, prednisolone, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporin.

A preferred embodiment of the composition in accordance with the present invention comprises one or more discrete dose units, each comprising the drug suitable for the treatment of an inflammation in a dose less than 250 mg.

According to the present invention, the regular therapeutically effective dose of the drug suitable for the treatment of an inflammation is as known in the field of the art. For example, the regular therapeutically effective dose of mesalamine is 4 g per day. Therefore, the drug suitable for the treatment of an inflammation of the composition in accordance with the present invention is in a dose preferably less than 4 g per day; more preferably, from 250 mg to 4 g per day; most preferably, from 250 mg to 1 g per day.

While the invention has been described in conjunction with a specific best mode, it is to be understood that many alternatives, modifications, and variations will be apparent to those skilled in the art in light of the foregoing description. All matters set forth herein or shown in the accompanying drawings are to be interpreted in an illustrative and non-limiting sense.

DETAILED DESCRIPTION OF THE PREFERRED EMBODIMENTS

Example 1

The Adhesion of HA in Colon Tissue (IVIS Image System-Vision 3)

Procedure:

1. 0.25 g High molecular weight sodium hyaluronate powder (HHA; Mw: 2 MDa; Freda) and 0.25 g low molecular weight sodium hyaluronate powder (LHA; Mw: 0.35 MDa; Freda) were added into 50 ml PBS buffer (Phosphate buffered saline) respectively to form a 0.5% solution, and then stirred for 6 hours until the powder was totally dissolved.

0.05 g LHA powder and 0.2 g HHA powder (ratio 2:8; MHA, medium molecular weight sodium hyaluronate powder) were added into 50 ml PBS buffer, and then stirred for 6 hours until the powder was totally dissolved.

2. Fluorescent HA (HA-f) was prepared by (1) 0.39 g MES free acid (2-(N-morpholino) ethanesulfonic acid, Calbiochem) and was dissolved in 100 ml dd water. (2) Solution A: 65 mg fluroresceinamine powder, (isomer I, Fluka) was dissolved in 9 ml 95% EtOH solution and then stirred for 10 minutes under a condition that light was prohibited. (3) Solution B: 359 mg EDC powder (N-(3-Dimethylamino propyl)-N-ethyl carbodiimide hydrochloride, Sigma) was dissolved in 9 ml MES buffer and then stirred for 10 minutes. (3) Solution C: 216 mg NHS powder (N-Hydroxysuccinimde, Sigma) was dissolved in 9 ml MES buffer and then stirred for 10 minutes. (4) 3 ml Solution A was slowly dropped into 50 ml 0.5% HA solution and then stirred for 10 minutes under a condition that light was prohibited. (5) 3 ml Solution B and 5 ml Solution C were separately dropped into the solution of step (4) and then stirred for 10 minutes under a condition that light was prohibited. (6) 0.02 M MES buffer was slowly added into the solution of step (5) until the volume reached 100 ml and then stirred for 24 hours at room temperature under a condition that light was prohibited. (7) The product after reaction was poured into a dialysis tubing (MW: 12000~14000) in 5 L dd water as a dialysis solution and then stirred for 5 days at 4 under a condition that light was prohibited with dialysis solution being changed every 12 hours until the dialysis solution had no fluorescence. (8) The liquid after dialysis was allocated into 50 cc plastic centrifuge tubes and then reserved at −20° C. refrigerator overnight followed by drying in a freeze-drying machine under a condition that light was prohibited. (9) The dried HA-f powder was reserved at −20° C. refrigerator. (10) 50 mg HA-f powder was slowly added into 10 ml PBS buffer and then stirred for 6 hours until the powder was totally dissolved.

3. Colon tissue of SD-rat (Sprague-Dawley Rat) aged 7-8 weeks was cut by scalpel and then washed by PBS buffer followed by being cut to 3-4 cm long with soaking in PBS buffer finally.

4. Injured colon tissue was prepared by brushing by toothbrush for 20 times longitudinally and then soaking in PBS buffer.

5. Normal and injured colon tissues were put into 12-well plates and then 1 ml 0.5% HA-f solution was added into each well and shaken for 2 hours at room temperature. Surplus HA-f solution was sucked by tip 2 hours later, and then soaked into PBS buffer for 10 minutes followed by removing PBS buffer repeatedly for 3 times.

6. Cleaned colon tissue was placed in a 12-well plate with lining tissue upwards and then placed onto the dock of the IVIS (in vivo image system, XENOGEN). The default parameter was set up as GFP (green fluorescent protein) whereas the excitation was 465 nm and the emission was 500 nm and then the image was captured by software.

7. All values in the table are expressed as means of n observations. The histological index was analyzed by Student's t-test.

Result:

The fluorescent index was quantified and arranged as in FIG. 2. The fluorescent index of normal colon tissue was defined as 1. The other colon tissues tests were calibrated by the defined value. The result showed that the HAs with the same average Mw were absorbed in the injured colon tissues obviously higher than in the normal colon tissues (P<0.01). In comparing the difference between HAs of three different average molecular weights absorbed in the injured colon tissues, the fluorescent index of absorption of 350 KDa HA by the injured colon tissues was obviously higher than those of the other two HAs of the other two average molecular weights (2 MDa and 1 MDa). Further, the fluorescent index of absorption of 1 MDa HA by even normal or injured colon tissues was higher than that of 2MDa HA.

Example 2

Comparative Study of Colon Tissue Concentration of Mesalamine after Intraluminal Instillation of Different Mesalamine Preparations Procedure:

1. experimental animals: 8-week-old male SPF-grade Sprague-Dawley rats (280~330 g) were supplied by Bio-LASCO Taiwan Co. Ltd.

2. Test samples: A: Colasa® enema (20 mg/ml' United Biomedical, Inc. Asia), B: 0.25% (w/w) HA mixture (8:2=2000 KDa HA: 350 KDa HA) in PBS (pH7.4) containing 5 mg/mL mesalamine (HA-M).

3. Intraluminal instillation of test samples: after lightly anesthetized by Zoletil 50, rat ventral incision was made by surgical scissors, colon was identified, 2 segments of colon (2 cm each) were tied by cotton threads, 0.5 ml of test samples were injected into the lumen of isolated colon segments, after 0.5, 1, 1.5, or 2 hours, rats were sacrificed and colon segments were removed. For each time point of intraluminal instillation, three rats were used.

4. Preparation of specimens: tissue biopsies were washed with PBS to remove the surface contamination, weighed and immediately frozen in liquid nitrogen and stored at −80° C. until use. Biopsies were crushed and 50 mM $KH_2PO_4$ solution (pH 7.4) was added. Tissue cells were disrupted ultrasonically using a microprobe inserted into the suspension for 10 seconds, and then ultrasonic disruption was stopped for 20 seconds at 25 W for a total of 10 minutes. After mixing by Vortex, samples stood for 30 minutes at room temperature, to permit protein precipitation, and were then centrifuged at 13000 g for 30 minutes.

5. Analysis of mesalamine concentration in colon tissue biopsies:mesalamine was measured by ultra performance liquid chromatography (UPLC). The method has been validated. Waters (UK) ACQUITY system and fluorescence detector (excitation 315 nm, emission 430 nm) were employed and the data were analyzed using Empower 2. An ACQUITY column (C18, 100×2.1 mm internal diameter, 1.7 um particle) purchased from Waters (UK) was protected by a Van (Waters) guard column (C18, 5×2.1 mm internal diameter, 1.7 um particles). The mobile phase consisted of 0.1 M acetic acid with triethylamine at pH 4.3 and acetonitrile (850:150). The flow-rate was 0.2 mL/min, with a resulting pressure of 5400 psi, and the analysis was performed at 40. Injection volume was 5 ul. Samples were derivatized using propionic anhydride to enhance the fluorescence characteristics of mesalamine. Triethylamine was used as an ion-pairing agent to improve peak symmetry. The UPLC method of mesalamine analysis was validated for measuring mesalamine over a nominal linear range of 10 to 1000 ng/ml. The linear correlation coefficient (R2) of the method used in this study is 1.00.

Results:

The (median) concentration of mesalamine in colon tissue biopsies after instillation of Colasa® peaked after one hour instillation. After that, the concentration of mesalamine dropped rapidly. On the contrary, HA-M continuously released mesalamine during the two-hour period and the concentration of mesalamine was rising and much higher than that of Colasa® after two-hour instillation (FIG. 3). The result of the present invention disclosed that HA-M sustained the release of mesalamine much longer as compared to the commercial mesalamine enema (Colasa®); however, it contained only one-fourth the concentration of mesalamine in Colasa®.

Example 3

The Comparative Effect of Administering HA and HA-Mesalamine (HA-M) on Lowering Down the Inflammation of Inflammatory Bowel Disease (IBD)

Procedure:

1. Test purpose: to induce the IBD in the SPF grade SD (Sprague-Dawley) rats with the TNBS in order to evaluate the comparative effect of administering HA and HA-M on lowering down the inflammation.

2. Test objective: HA mixture, comprising LMWHA and HMWHA, whereas the HMWHA was 2 million Da and the LMWHA was 1 million Da and 350 kilo Da, mixed in the mixing ratio of 8:2 by weight which were categorized into group C and group D, respectively, and dissolved in PBS solution to produce a concentration of 0.0625% (w/v).

3. Method: (1) Test target: Rats aged 8 weeks were selected, and classified into four groups: group A was treated by PBS, group B was treated by Colasa® (20 mg mesalamine/mL), group C represented HMWHA:LMWHA of 2 M Da:1 M DA in the mixing ratio of 8:2, group D represented HMWHA:LMWHA of 2 M Da:350 k Da in the mixing ratio of 8:2. Each group consisted of 10 rats. (2) Animal test: all rats of the treating group were fasted for 2 days; in test day 1, the rats were anesthetized for administrating 1 ml of TNBS (50 mg/mL) via the rectum; through test days 5 to 8 and days 10 to 13, administering 1 ml of different test agents of mesalamine (M) and two categories of HA-Ms via the rectum in groups B, C and D everyday; in test day 9, half rats of each group were sacrificed to observe and record changes of body weight and the inflammation area. And the other half of the rats were sacrificed to observe and record changes of body weight and the inflammation area in day 14. All rats of the control group were fasted for 2 days; in test day 1, the rats were anesthetized for administrating 1 ml of TNBS (50 mg/mL) via the rectum; in test days 5 to 8 and days 10 to 13, administering 1 ml of PBS via the rectum in group A everyday; in test day 9, half the rats were sacrificed to observe and record changes of body weight and the inflammation area. And the other half of the rats were sacrificed to observe and record changes of body weight and the inflammation area in day 14.

Result:

1. inflammatory index: the present invention used changes of body weights and average inflammation area as an index to view the amelioration of IBD.

2. The trend of body weight changes showed that groups B, C and D had a better relief effect on IBD than group A through day 3 to day 14 (FIG. 4). Especially through days 12 to 14, the body weight changes in all three treating groups were statistically more significant than that in group A. Also, the recovery rate of the inflammation was better in three treating groups than that in the control group in test day 14 (D14) (FIG. 5). Because the amount of mesalamine of the HA-M formulation of the present invention was 4 times less than regular therapeutically effective dose of Colasa®, the result of the present invention indicated that only one-fourth of the normal dose (i.e. the routine administrating dose of the referenced drug) could achieve almost the same treating effect as the referenced drug.

What is claimed is:

1. A method for treating a mammal or human suffering from mucosal inflammation related disorder, comprising administering to said mammal or human a drug suitable for the treatment of mucosal inflammation and a therapeutically effective dose of a hyaluronic acid (HA) mixture which comprises at least two hyaluronic acids including a low average molecular weight HA (LMWHA) and a high average molecular weight HA (HMWHA), wherein said drug is mesalamine, and a dose of said drug is from 250 mg to 1 g per day, wherein the mucosa of the mucosal inflammation is the mucosa of a gastrointestinal tract; wherein the HA mixture is of an average molecular weight (MW) between 50 kilo Dalton and 5 million Dalton; wherein the mixing ratio of the HA mixture and mesalamine is 0.625:5 by weight; wherein the average MW of the LMWHA is between 50 kilo Da and 1.5 million Da, and the average MW of the HMWHA is between 1.5 million Da and 5 million Da, wherein the LMWHA and the HMWHA are apart from each other by at least 0.5 million Da, and wherein the mixing ratio of the LMWHA and the HMWHA is 20:80 by weight.

2. The method of claim 1, wherein the mucosal inflammation related disorder is gastritis, enteritis, peptic ulcer, inflammatory bowel disease (IBD), Crohn's Disease, irritable bowel syndrome (IBS), intestinal inflammation or eosinophilic gastroenteritis.

3. The method of claim 1, wherein the drug and the HA mixture further comprise an excipient to formulate an administrating dosage form for the gastrointestinal tract.

4. The method of claim 3, wherein the administrating dosage form for gastrointestinal tract use is selected from the group consisting of solid dosage form, perfusion, enema, suppository, solution, and suspension.

5. The method of claim 4, wherein said solid dosage form is a controlled release tablet.

6. The method of claim 4, wherein said solid dosage form is an enteric coated capsule.

* * * * *